United States Patent [19]

Pfeiffer

[11] Patent Number: 5,691,539
[45] Date of Patent: Nov. 25, 1997

[54] INTRAORAL SENSING DEVICE TO BE PLACED INTO THE MOUTH OF A PATIENT FOR PRODUCING TOOTH AND JAW IMAGES

[76] Inventor: Manfred Pfeiffer, 18, Warrington Crescent, GB - London W9 1EL, Great Britain

[21] Appl. No.: 637,326

[22] Filed: Apr. 22, 1996

[30] Foreign Application Priority Data

Apr. 22, 1995 [DE] Germany ............... 295 06 839 U

[51] Int. Cl.⁶ .................. A61B 6/14; G01T 1/24
[52] U.S. Cl. ..................... 250/370.09; 378/191
[58] Field of Search ............. 250/370.09; 378/98.8, 378/191

[56] References Cited

U.S. PATENT DOCUMENTS

| | | | |
|---|---|---|---|
| 4,593,400 | 6/1986 | Mouyen | 378/98.8 |
| 4,987,307 | 1/1991 | Rizzo et al. | 250/370.09 X |
| 5,331,166 | 7/1994 | Yamamoto et al. | 250/370.09 X |
| 5,434,418 | 7/1995 | Schick | 378/191 X |
| 5,510,623 | 4/1996 | Sayag et al. | 250/370.09 X |

FOREIGN PATENT DOCUMENTS

| | | |
|---|---|---|
| 9419116 | 3/1995 | Germany. |
| 9319391 | 4/1996 | Germany. |
| 9222874 | 12/1992 | WIPO. |
| 9310709 | 6/1993 | WIPO. |

OTHER PUBLICATIONS

Trophy RVG–PC, STV–PC Dental Imaging (1994).
Handbuch "Sens–A–Ray" (1993).

*Primary Examiner*—Edward J. Glick
*Attorney, Agent, or Firm*—Robert W. Becker & Associates

[57] ABSTRACT

An intraoral sensing device for producing tooth and jaw images of a patient has a housing with a back. The housing has an interior. An image sensor is positioned in the interior of the housing. A printed circuit board with electrical contacts is positioned in the interior of the housing and connected to the image sensor. An electric cable, for connecting the sensing device to an image processing unit, is provided. It extend into the interior of the housing at a location of entry and has electrical leads. The electrical leads are connected to the electrical contacts of the printed circuit board. The electric cable extends from the location of entry at the housing at an angle of 0° to 10° relative to the back.

9 Claims, 2 Drawing Sheets

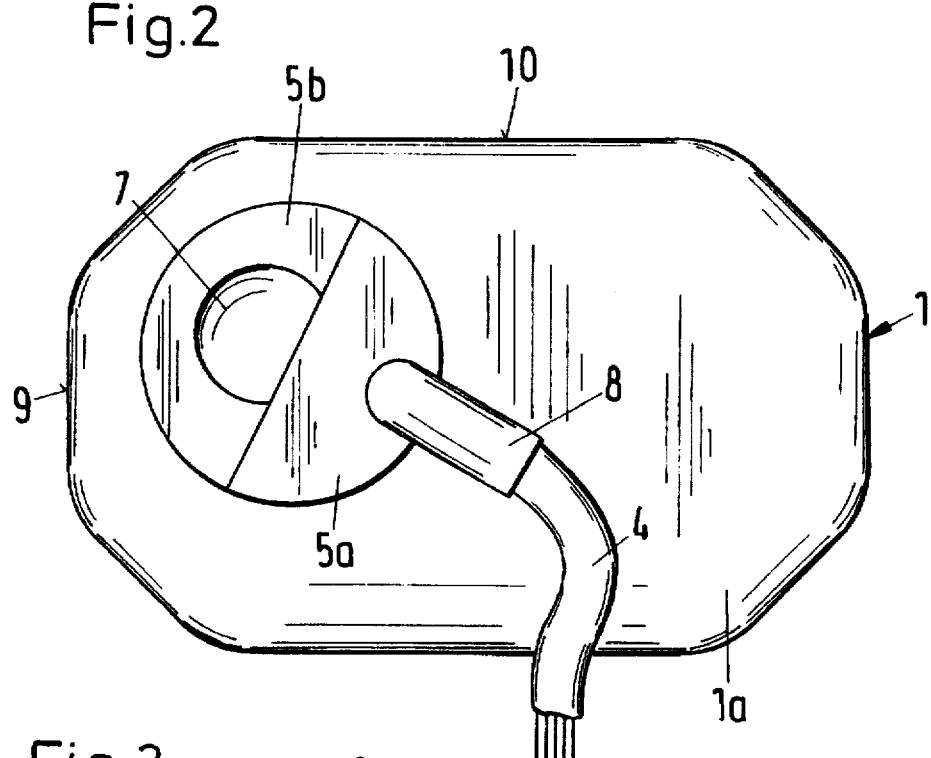
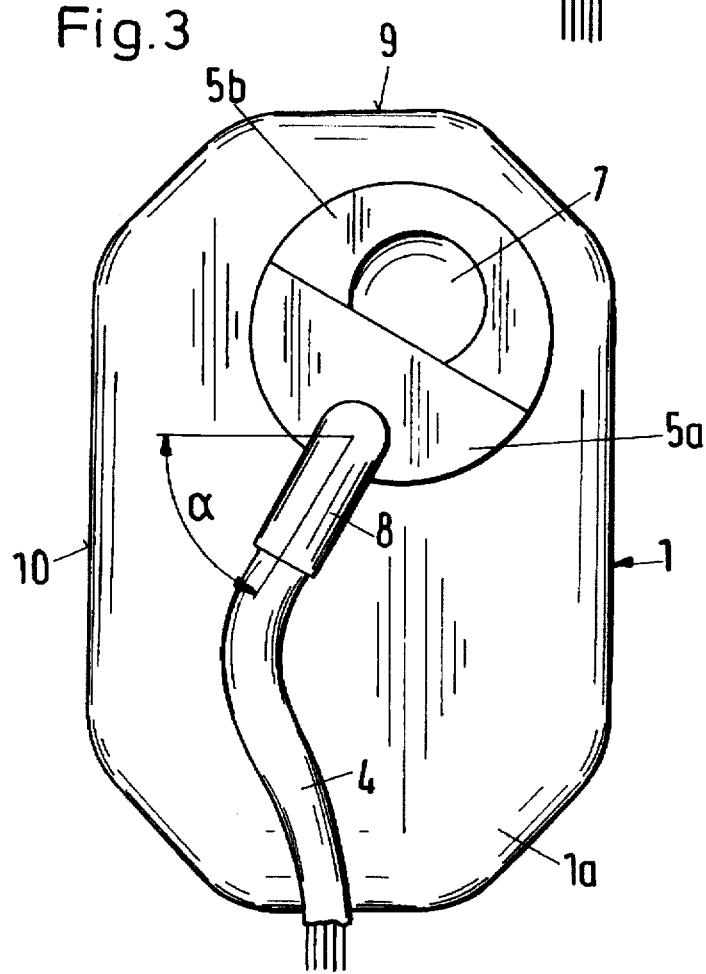

INTRAORAL SENSING DEVICE TO BE PLACED INTO THE MOUTH OF A PATIENT FOR PRODUCING TOOTH AND JAW IMAGES

BACKGROUND OF THE INVENTION

The present invention relates to an intraoral sensing device to be placed into the patient's mouth for producing tooth and jaw images of a patient, wherein the sensing device comprises a narrow, conventionally rectangular housing for receiving at least one image sensor and a coordinated printed circuit control board to which are connected diverse electrical leads of an electric cable which exits at the back of the housing and which is connectable to an image processing unit.

Such intraoral sensing devices are, for example, known from German Gebrauchsmuster 93 19 391. This document also refers to further prior art, for example, printed documents with the title "Visualix the new way to take a dental X-rays" of the firm Philips Medical Systems and "SENS-A-RAY a revolution in dental radiography" of the firm Regam Medical Systems AB. The connecting electrical cable in these known devices exits from the housing either on the narrow end face of the housing or at a right angle to the back of the housing.

Both embodiments, with respect to the positioning of the sensing device in the oral cavity of the patient, are disadvantageous, especially when images of the incisors or of the rearward molar area are to be produced. On the one hand, the cable guiding is said to be uncomfortable for the patient, when the sensor is positioned at the tooth of which an image is to be taken, on the other hand, it is said that the connecting electrical cable extending from the patient's mouth is bent to a degree that is not tolerable.

Essentially the same disadvantages have also been reported for the intraoral sensing device that is disclosed in the Gebrauchsmuster 93 19 391. The connecting electrical cable is guided at an angle between 30° and 60° relative to the plane of the back of the housing which is also uncomfortable for the patient.

It is therefore an object of the present invention to provide an improved intraoral sensing device that is more comfortable for the patient.

SUMMARY OF THE INVENTION

The intraoral sensing device for producing tooth and jaw images of a patient according to the present invention is primarily characterized by:

a housing with a back, the housing having an interior;

an image sensor positioned in the interior of the housing;

a printed circuit board with electrical contacts positioned in the interior of the housing and connected to the image sensor;

an electric cable, for connecting the sensing device to an image processing unit, extending into the interior of the housing at a location of entry and comprising electrical leads, the electrical leads connected to the electrical contacts of the print circuit board; and the electrical cable extending from the location of entry from the housing at an angle of 0° to 10° relative to the back.

Preferably, the back of the housing at the location of entry comprises a convex portion, wherein the electric cable has an end from which the electrical leads project, and wherein the convex portion covers at least the end of the electric cable with the electrical leads projecting therefrom.

Advantageously, the convex portion is a cap formed as a unitary part of the back, the cap being divided into a first and a second part, wherein, when positioned in the mouth of the patient, the first part is below the second part and the location of entry is at the first part.

Preferably, the end of the electric cable is sealingly glued to the first part of the cap.

In preferred embodiment of the present invention, the convex portion has a depression for accommodating a finger of the patient to allow for correct and secure positioning of the sensing device.

Advantageously, the convex portion is positioned eccentric to a center of the back of the housing.

In preferred embodiment of the invention, the intraoral sensing device further comprises a reinforcement sleeve surrounding a portion of the electric cable positioned exterior to the housing adjacent to the location of entry.

Preferably, the housing has two longitudinal end faces and two transverse narrow end faces.

Advantageously, the electric cable extends at an angle of between 30° to 60° relative to the longitudinal end faces and the transverse narrow end faces.

According to the present invention, the electric cable extends from the back of the housing at an angle between 0° and 10° relative to the plane of the back.

With such an intraoral sensing device it is possible to provide an optimal positioning of the sensing device for almost any desired tooth image or jaw image, without the cable guiding being uncomfortable to the patient.

Advantageously, the housing at the location of entry of the electric cable is provided with a convex portion which may be in the form of a unitary cap formed at the housing. Within this convex portion it is possible to house the connecting electrical leads without increasing the size of the housing. The convex portion serves at the same time as a positioning aid for the patient for resting the sensing device at the tooth or jaw portion of which an image is to be taken.

It is especially advantageous when the connecting electric cable in the area of the location of entry is surrounded by an elastic reinforcement sleeve. The bending of the electric cable, which is unavoidable during use of the sensing device, thus does not result during the service life of the sensing device in fatigue of the electric cable and cable breakage.

In a preferred embodiment of the intraoral sensing device the housing is substantially rectangular with two narrow and two longitudinal end faces. In this manner, the intraoral sensing device can be used for images in the so-called portrait format as well as for images in the so-called landscape format.

It is further suggested with the present invention that the electric cable relative to the end face of the housing extends at an angle between 30° and 60°. In this manner, for images in the landscape format as well as in the portrait format a uniformly suitable cable guiding is ensured which results only in minimal bending for both applications.

BRIEF DESCRIPTION OF THE DRAWINGS

The object and advantageous of the present invention will appear more clearly from the following specification in conjunction with the accompanying drawings, in which:

FIG. 2 shows a view of the back of the intraoral sensing device with cable guiding for images in the landscape format; and FIG. 3 shows a view of the back of the intraoral senor with cable guiding for images taken in the portrait format.

DESCRIPTION OF PREFERRED EMBODIMENT

Figure 1:
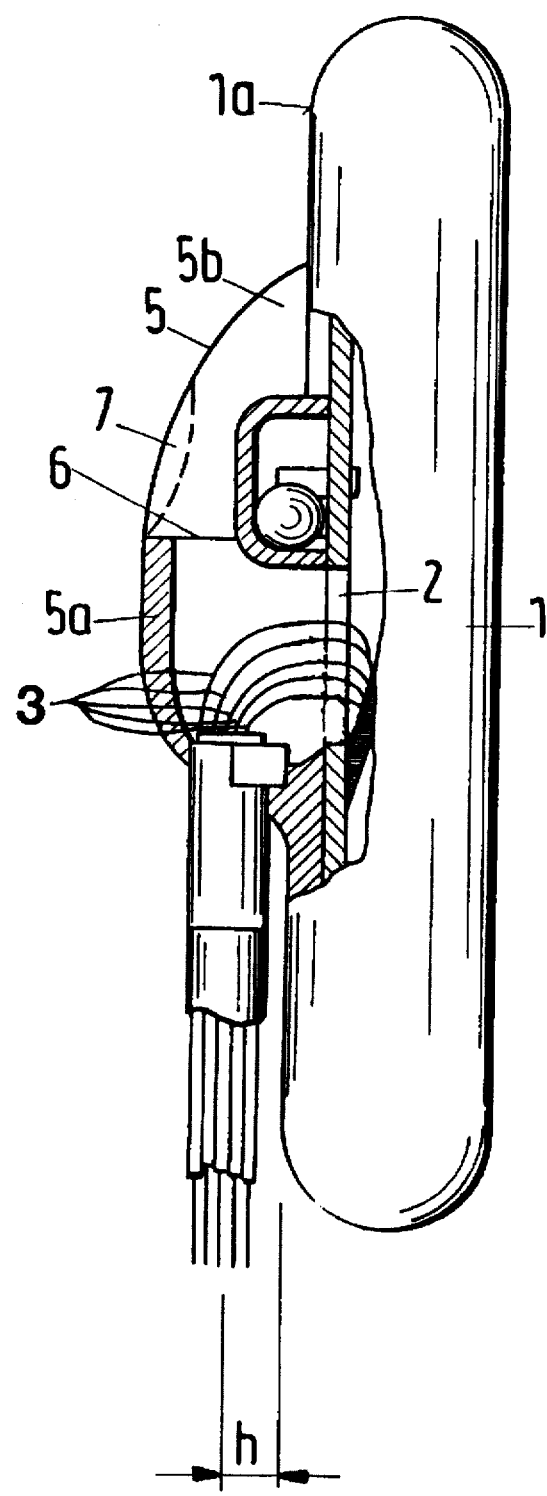
FIG. 1 shows in a side view, partly in section, an embodiment of the inventive intraoral sensing device.

The present invention will now be described in detail with the aid of several specific embodiments utilizing FIGS. 1 through 3.

The housing 1 which in a plan view is substantially rectangular, contains a non-represented image sensor (CCD sensor) which is connected in a suitable manner to the printed circuit control board 2. To the printed circuit control board 2 which comprises electronic components which are not specified here, electrical leads 3 projecting from an electric cable 4 entering the housing are connected, whereby the electric cable, as mentioned before, is connected to a non-represented image processing unit.

The location of entry of the electric cable 4 is provided at the back 1a of the housing 1 whereby the electric cable 4 is guided at an angle which is substantially 0° to the longitudinal plane of the housing. As can be seen in FIG. 1, in the shown embodiment the electric cable 4 extends substantially parallel to the back 1a of the housing at a distance h. As can be seen in FIG. 1, the housing 1 in the area of the location of cable entry is provided with an eccentric convex portion which is formed by a cap 5 that is a unitary part of the housing. The cap 5 is divided in the transverse direction at the location indicated by reference numeral 6. The electric cable 4 is connected to the lower cap portion 5a so that no pulling forces are exerted on the cable. The electric cable 4 including the electrical leads 3 are glued to the cap 5 so as to be water-tight. Both cap parts 5a, 5b are also connected in a water-tight manner during final assembly.

Even though the convex portion 5 provides already for a good positioning aid for the patient during positioning of the sensing device at a tooth of which images are to be taken, it may be advantageous to provide at the upper cap portion 5b a concave depression 7 for a finger, as is indicated in a dashed line in FIG. 1.

The electric cable 4 in the area of location of entry at the cap 5 is enclosed by an elastic reinforcment sleeve 8. The reinforcment sleeve prevents that the connecting electric cable 4 is bent to a too great extent in this area.

As can be seen in FIGS. 2 and 3, the housing 1 is rectangular with two shorter end faces 9 and two longer end faces 10. FIG. 2 shows the guiding of the electric cable 4 when the intraoral sensing device is used for images in the landscape format. FIG. 3 shows the guiding of the electric cable 4 when using the intraoral sensing device in portrait format. In order to be able to guide the electric cable 4 in the downward direction away from the housing 1, the electric cable 4, relative to the end faces 9 of the housing 1, extends in an angle α of between 30° and 60°.

The present invention is, of course, in no way restricted to the specific disclosure of the specification and drawings, but also encompasses any modifications within the scope of the appended claims.

What I claim is:

1. An intraoral sensing device for producing tooth and jaw images of a patient, said sensing device comprising:

a housing with a back, said housing having an interior;

an image sensor positioned in said interior of said housing;

a printed circuit board with electrical contacts positioned in said interior of said housing and connected to said image sensor;

an electric cable, for connecting said sensing device to an image processing unit, extending into said interior of said housing at a location of entry at said back and comprising electrical leads, said electrical leads connected to said electrical contacts of said printed circuit board; and wherein said electric cable exits from said location of entry at said back from said housing at an angle of 0° to 10° relative to said back.

2. An intraoral sensing device according to claim 1, wherein said back of said housing at said location of entry comprises a convex portion, wherein said electric cable has an end from which said electrical leads project, wherein said convex portion covers at least said end of said electric cable with said electrical leads projecting therefrom.

3. An intraoral sensing device according to claim 2, wherein said convex portion is a cap formed as a unitary part of said back, said cap being divided into a first and a second part, wherein, when positioned in the mouth of a patient, said first part is below said second part and said location of entry is at said first part.

4. An intraoral sensing device according to claim 3, wherein said end of said electric cable is sealingly glued to said first part of said cap.

5. An intraoral sensing device according to claim 2, wherein said convex portion has a depression for accommodating a finger of the patient to allow for correct and secure positioning of said sensing device.

6. An intraoral sensing device according to claim 2, wherein said convex portion is positioned eccentric to a center of said back of said housing.

7. An intraoral sensing device according to claim 1, further comprising a reinforcement sleeve surrounding a portion of said electric cable positioned exterior to said housing adjacent to said location of entry.

8. An intraoral sensing device according to claim 1, wherein said housing has two longitudinal end faces and two transverse narrow end faces.

9. An intraoral sensing device according to claim 8, wherein said electric cable extends at an angle of between 30° to 60° relative to said transverse narrow end faces.

* * * * *